United States Patent
Kato et al.

(10) Patent No.: US 10,820,846 B2
(45) Date of Patent: Nov. 3, 2020

(54) STORAGE TRAY

(71) Applicant: Nikkiso Company Limited, Tokyo (JP)

(72) Inventors: Ryo Kato, Shizuoka (JP); Hiroshi Miyaji, Shizuoka (JP); Masatoshi Tarumi, Shizuoka (JP); Shigeaki Funamura, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 291 days.

(21) Appl. No.: 15/944,946

(22) Filed: Apr. 4, 2018

(65) Prior Publication Data

US 2018/0220946 A1   Aug. 9, 2018

Related U.S. Application Data

(63) Continuation of application No. PCT/JP2016/079613, filed on Oct. 5, 2016.

(30) Foreign Application Priority Data

Oct. 6, 2015   (JP) .................................. 2015-198489

(51) Int. Cl.
*A61B 5/15* (2006.01)
*A61M 5/00* (2006.01)
(Continued)

(52) U.S. Cl.
CPC ...... *A61B 5/150305* (2013.01); *A61B 5/1486* (2013.01); *A61B 5/14532* (2013.01);
(Continued)

(58) Field of Classification Search
CPC ........ A61B 5/150305; A61B 5/150229; A61B 5/150992; A61B 5/15; A61M 5/002; A61M 2209/06
(Continued)

(56) References Cited

U.S. PATENT DOCUMENTS 4,120,394 A * 10/1978 Soltes .................... A45C 11/16
                                                              206/19
4,479,761 A * 10/1984 Bilstad ................ A61M 1/3496
                                                          128/DIG. 12
(Continued)

FOREIGN PATENT DOCUMENTS

JP    2001253472 A    9/2001
JP    2013-245664    12/2013
(Continued)

OTHER PUBLICATIONS

International Search Report from the Japanese Patent Office for Application No. PCT/JP2016/079613 dated Dec. 27, 2016.
(Continued)

*Primary Examiner* — Rafael A Ortiz
(74) *Attorney, Agent, or Firm* — Young Basile Hanlon & MacFarlane, P.C.

(57) ABSTRACT

To provide a storage tray in which flexible tubes are to be stored and with which the efficiency of work to be performed after priming can be improved. A storage tray that stores a flexible tube to be attached to a medical apparatus, the flexible tube allowing fluid to flow therethrough. The storage tray includes a tray body that is securable to a predetermined portion of the medical apparatus and in which the flexible tube is storable, and a receiving portion that is included in the tray body and is capable of receiving a priming solution, which is used for flushing the flexible tube attached to the medical apparatus, and storing a predetermined volume of priming solution.

16 Claims, 10 Drawing Sheets

(51) Int. Cl.
 B65B 1/34 (2006.01)
 A61B 5/145 (2006.01)
 A61B 5/1486 (2006.01)
(52) U.S. Cl.
 CPC .. *A61B 5/150229* (2013.01); *A61B 5/150755* (2013.01); *A61B 5/150992* (2013.01); *A61M 5/002* (2013.01); *B65B 1/34* (2013.01); *A61M 2202/0021* (2013.01); *A61M 2202/0413* (2013.01); *A61M 2209/06* (2013.01); *A61M 2209/082* (2013.01); *A61M 2230/201* (2013.01)
(58) Field of Classification Search
 USPC ........ 206/364, 363, 560, 562, 564, 569–571
 See application file for complete search history.

(56) References Cited

U.S. PATENT DOCUMENTS

| | | | |
|---|---|---|---|
| 4,479,762 A * | 10/1984 | Bilstad | A61M 1/3496 |
| | | | 206/364 |
| 5,906,598 A * | 5/1999 | Giesler | A61M 5/1411 |
| | | | 206/564 |
| 5,996,634 A | 12/1999 | Dennehey et al. | |
| 2006/0011501 A1* | 1/2006 | Itou | A61M 25/002 |
| | | | 206/370 |
| 2009/0008306 A1 | 1/2009 | Cicchello et al. | |
| 2013/0177836 A1 | 7/2013 | Teutsch | |
| 2013/0178836 A1 | 7/2013 | Teutsch | |
| 2017/0049955 A1* | 2/2017 | Uber, III | A61M 5/1413 |

FOREIGN PATENT DOCUMENTS

| | | |
|---|---|---|
| WO | 1996/040320 A1 | 12/1996 |
| WO | 2005/042065 A2 | 5/2005 |
| WO | 2010/121819 A1 | 10/2010 |

OTHER PUBLICATIONS

Extended European Search Report, dated May 21, 2019, Application No. 16853619.1.

Chinese Office Action dated Mar. 12, 2020 from corresponding Chinese Application 201680058404.3.

\* cited by examiner

[ Fig. 1 ]
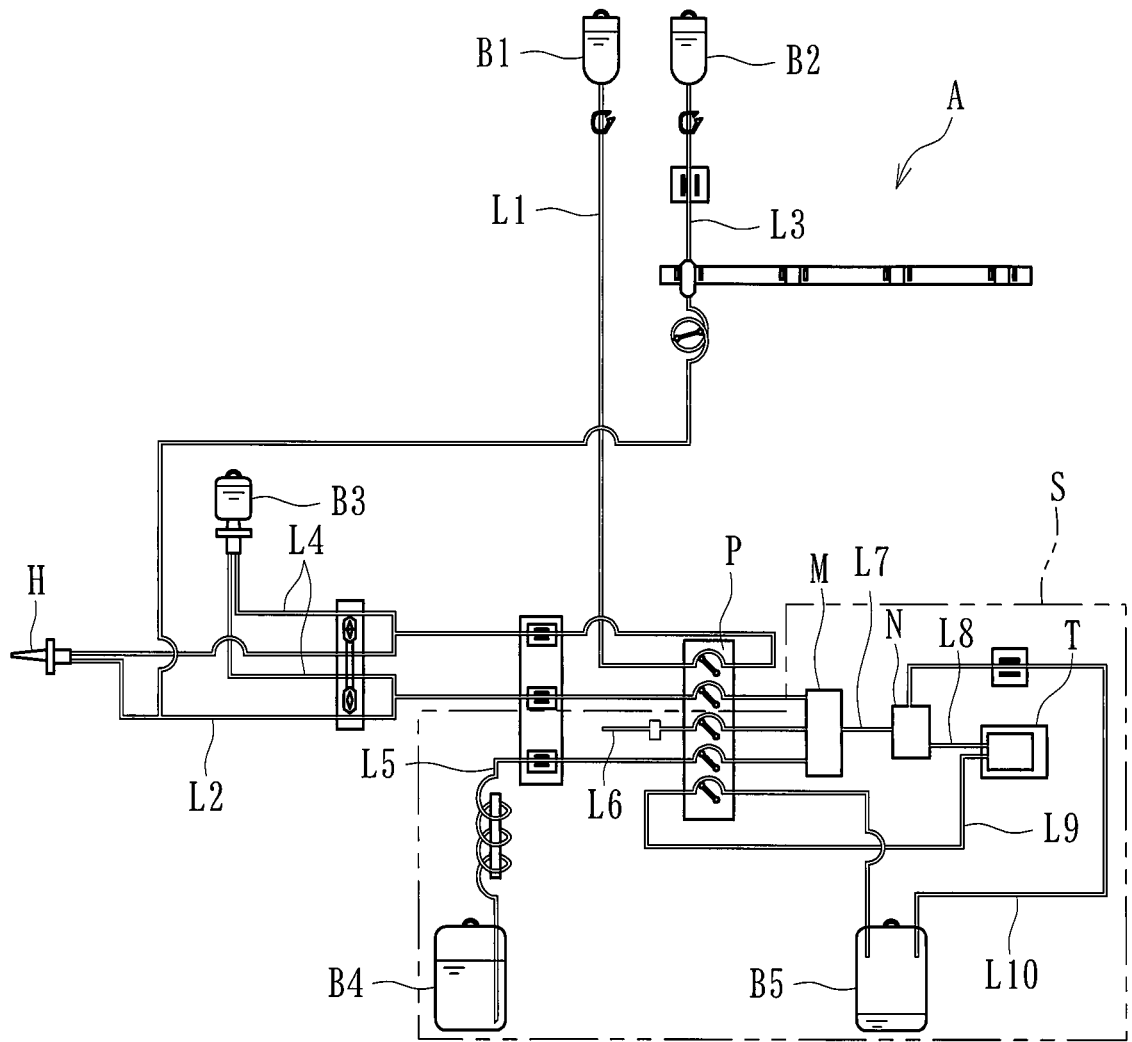
[ Fig. 2 ]
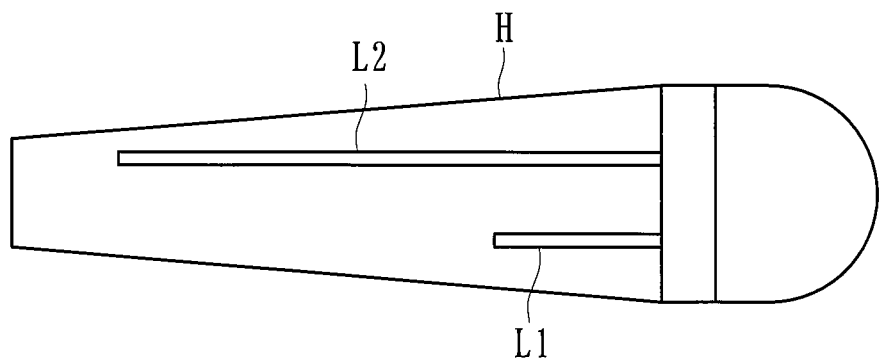

[Fig. 3]
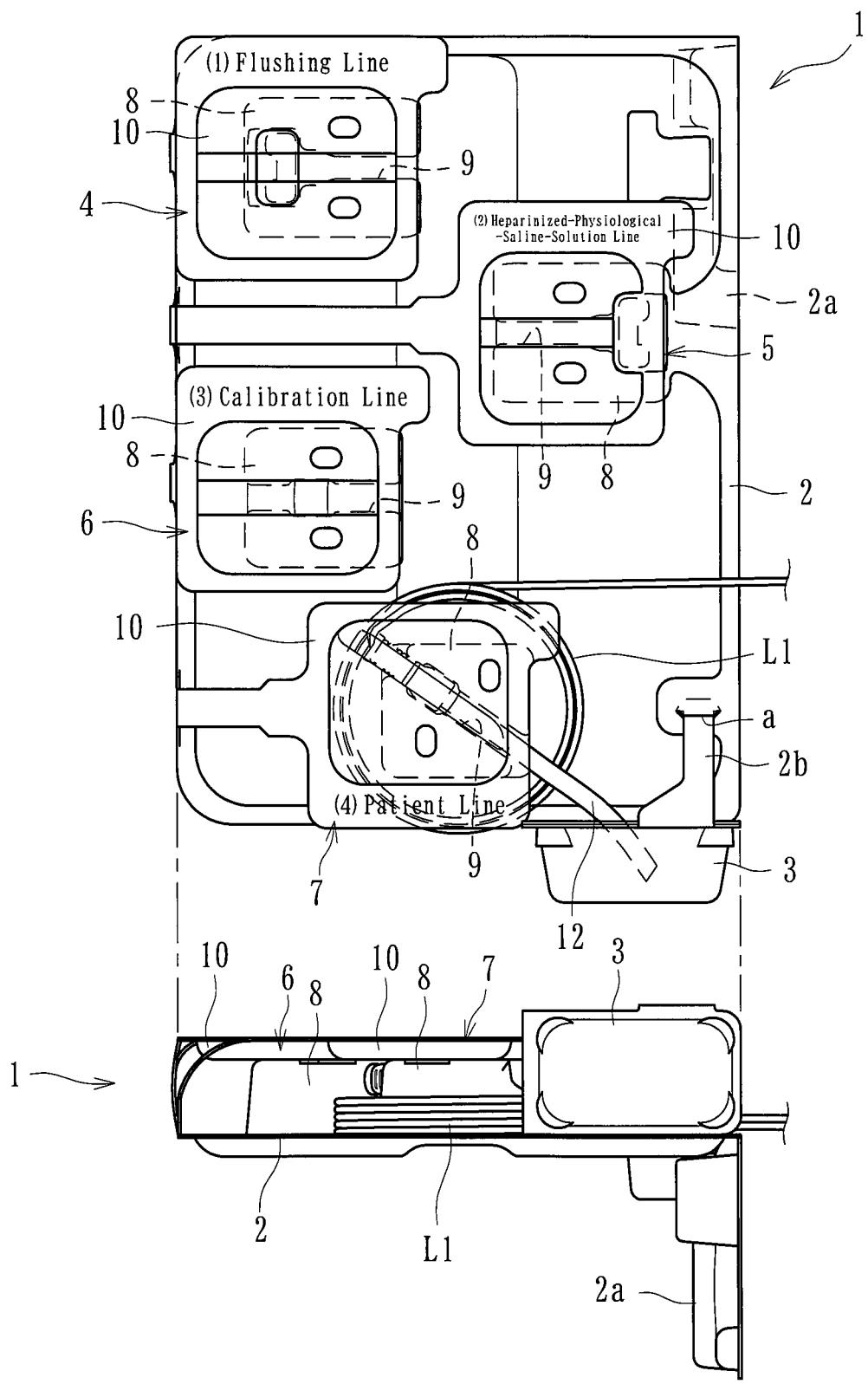

[Fig. 4]
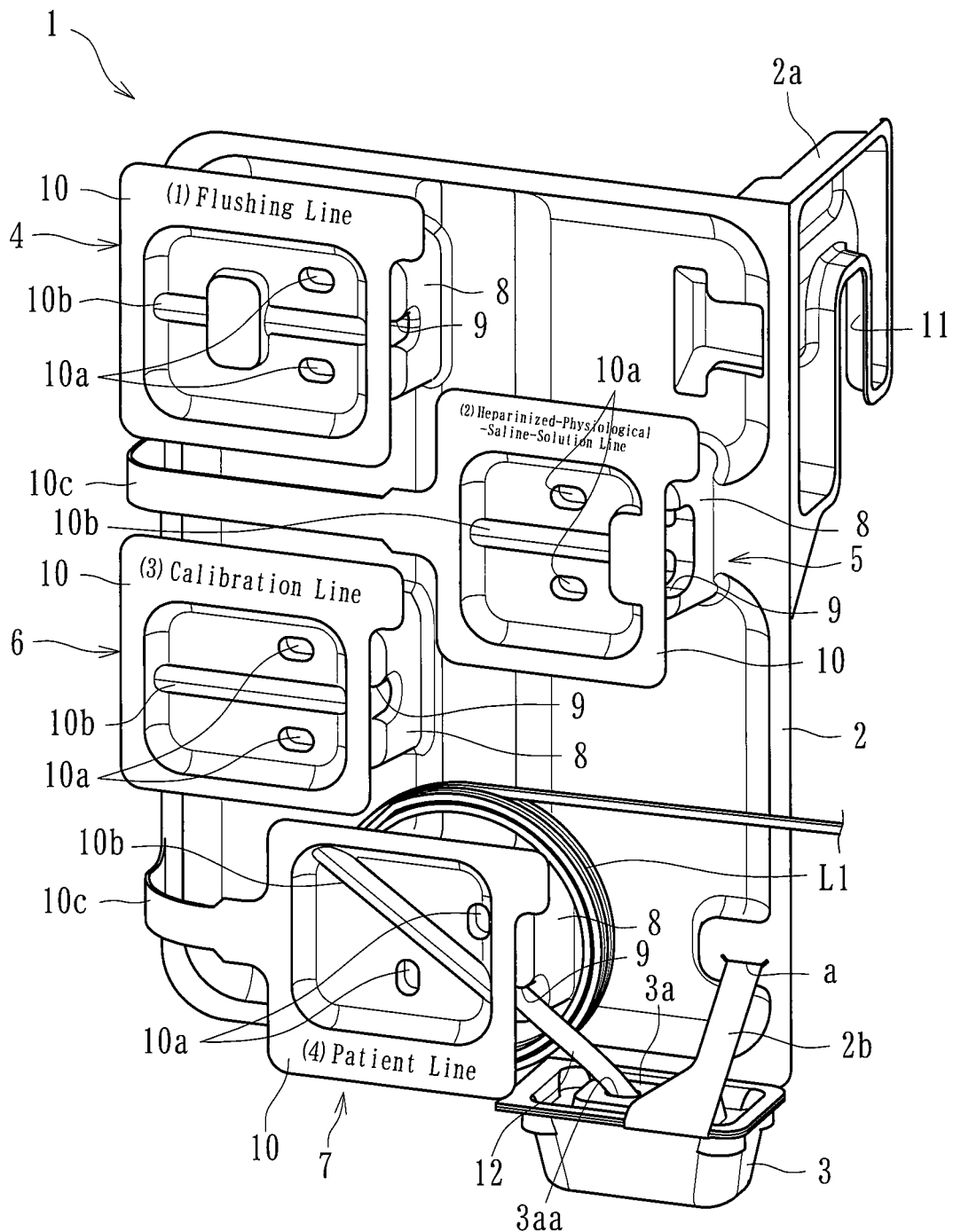

[Fig. 5]
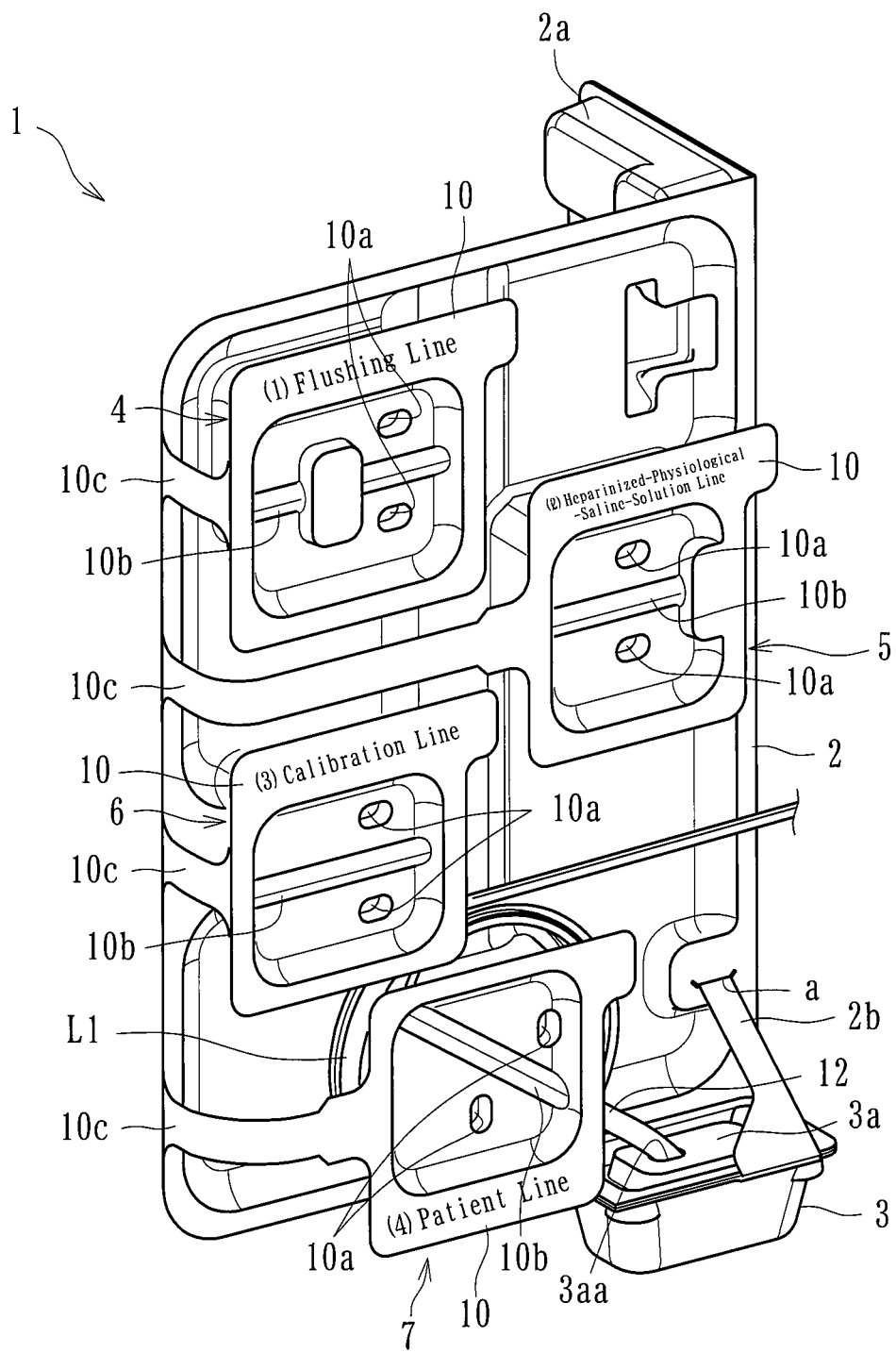

[Fig. 6]
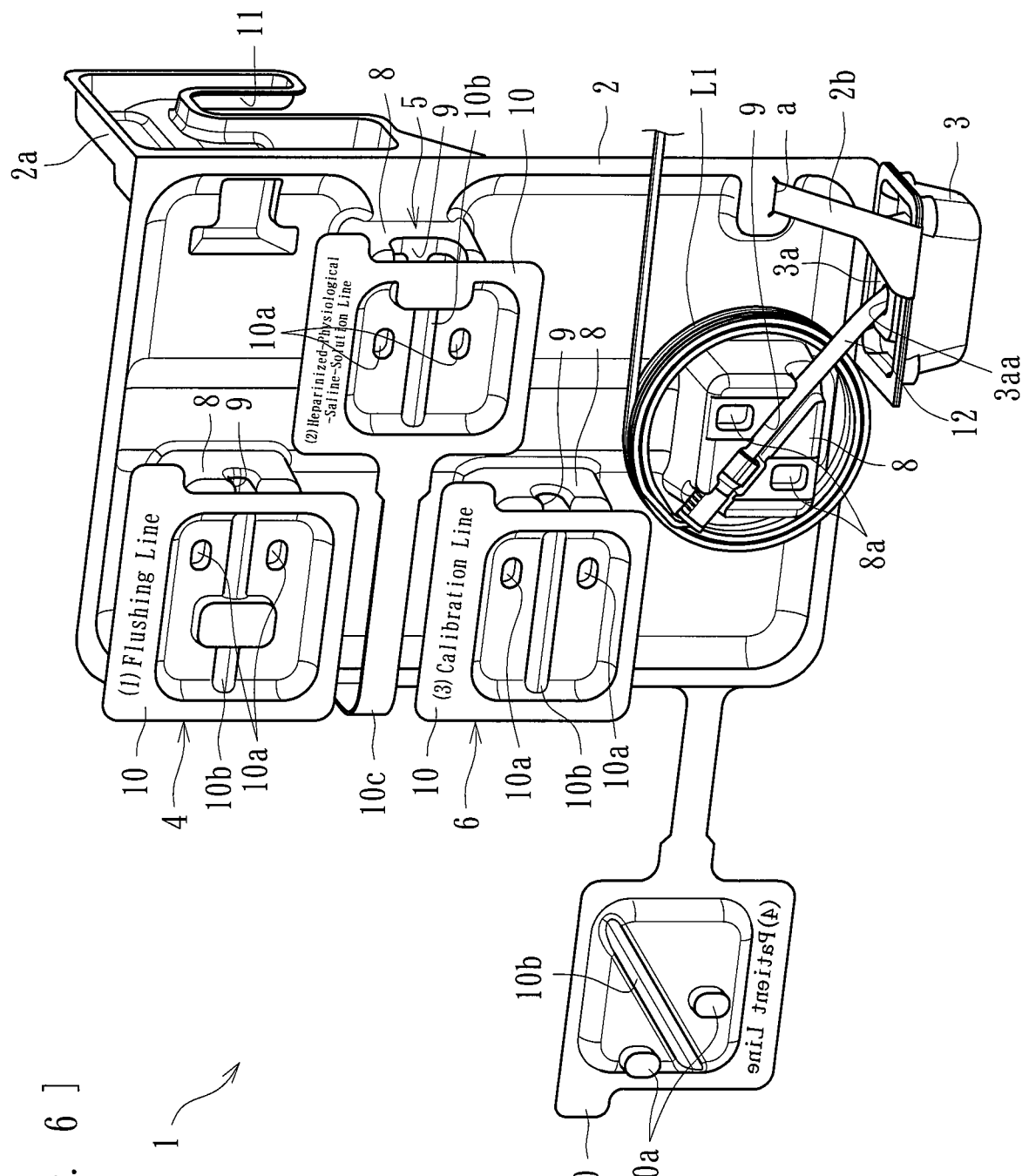

[ Fig. 7 ]
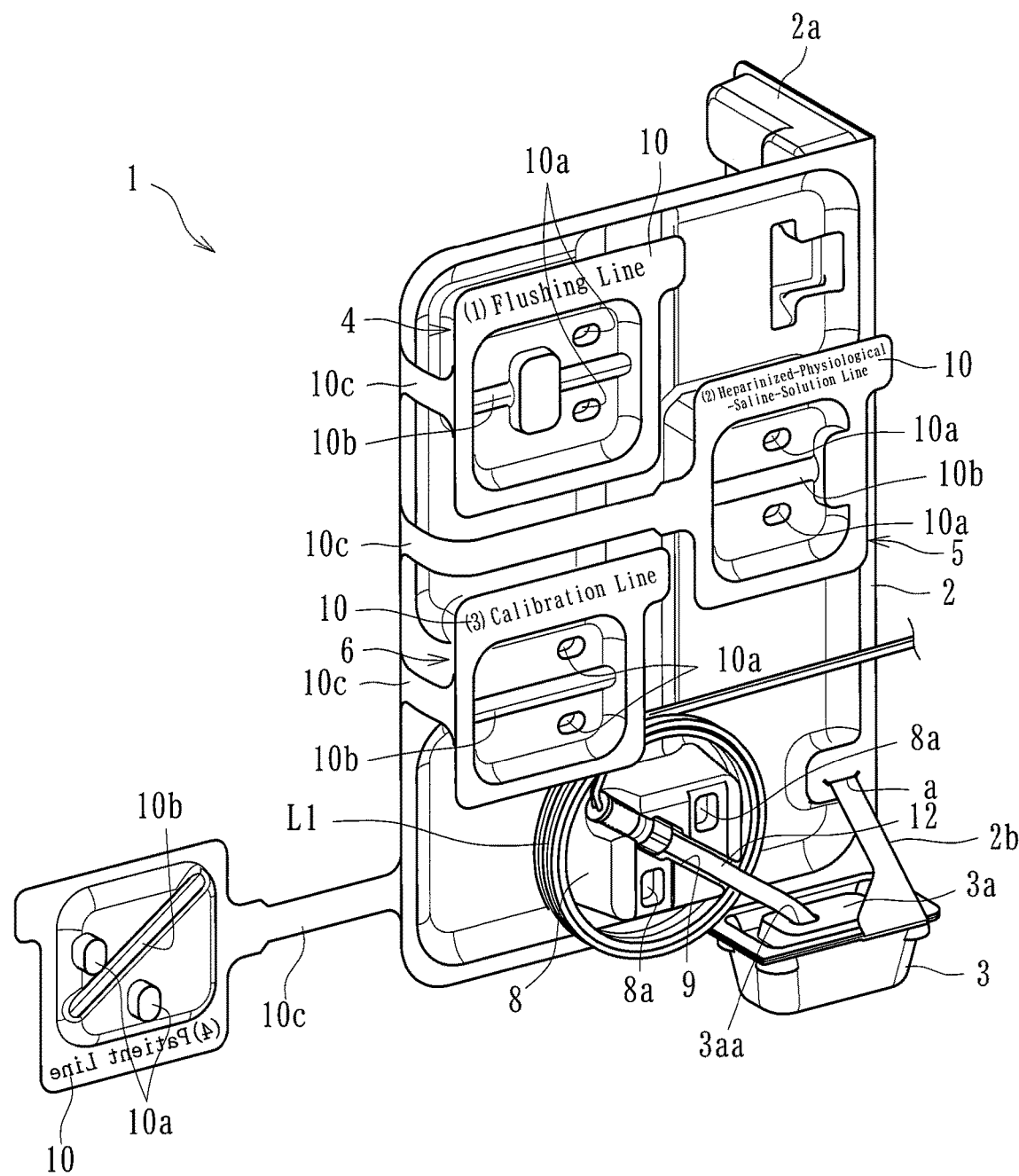

[Fig. 8]
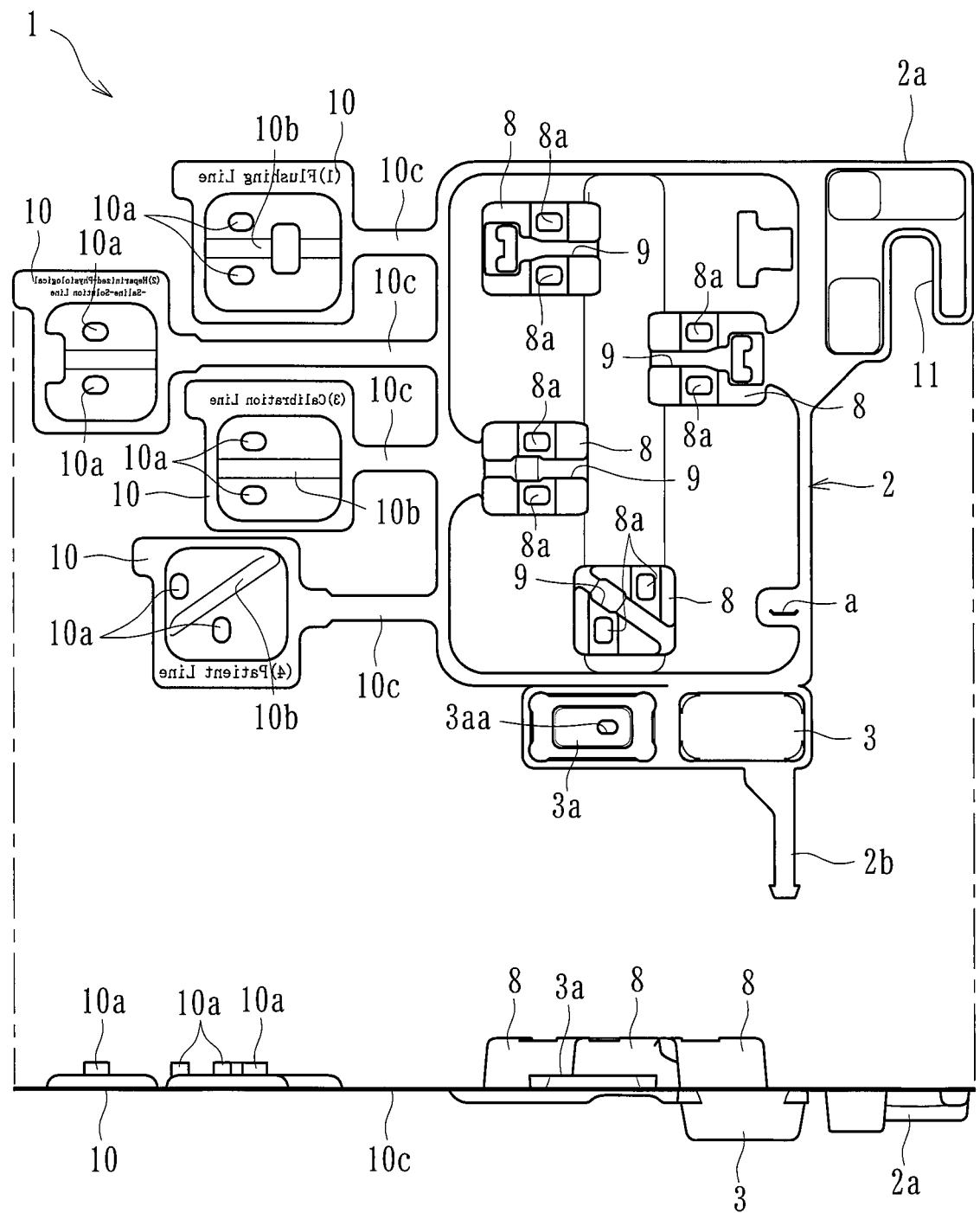

[Fig. 9]
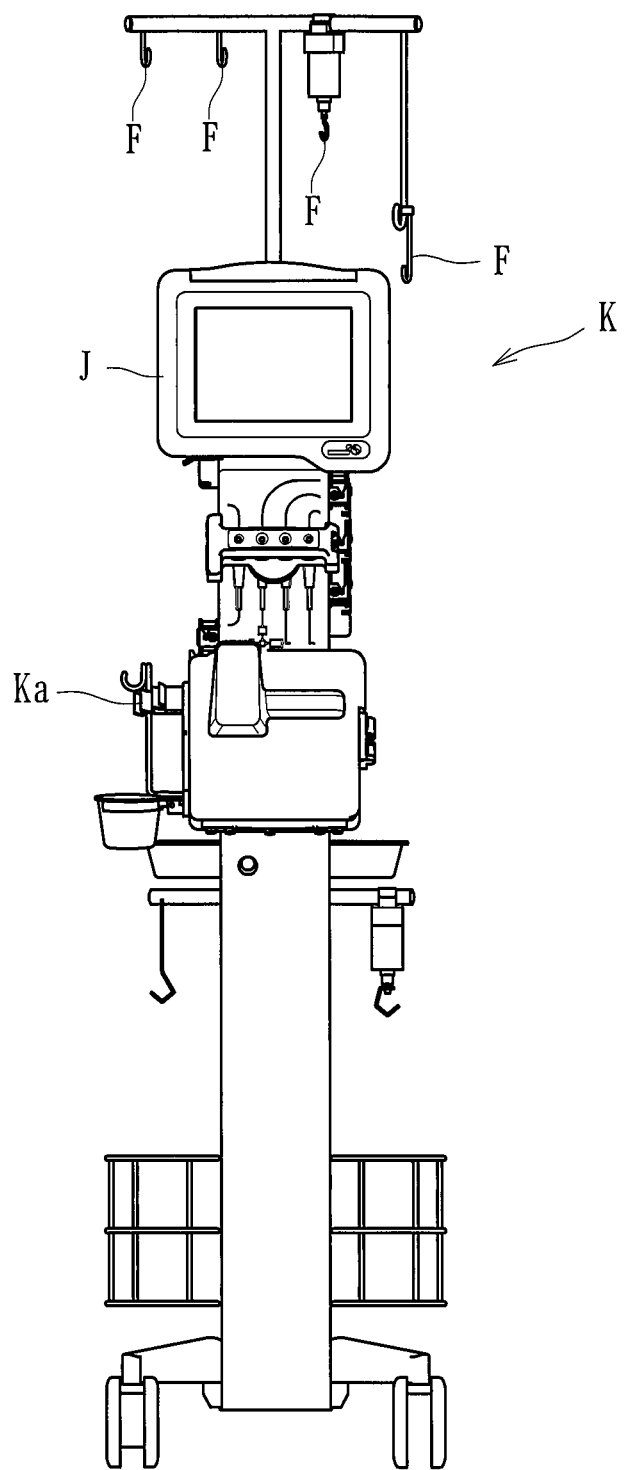

[Fig. 10]
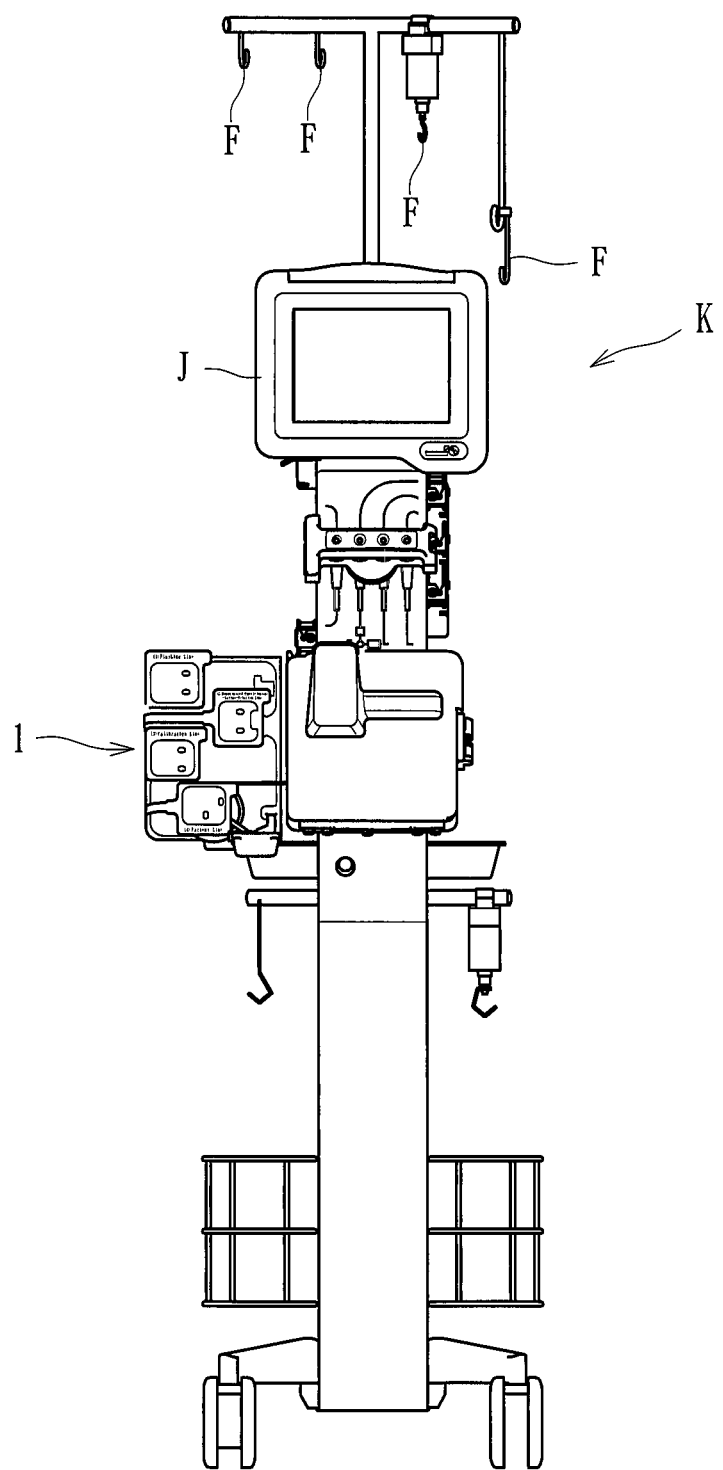

[ Fig. 11 ]
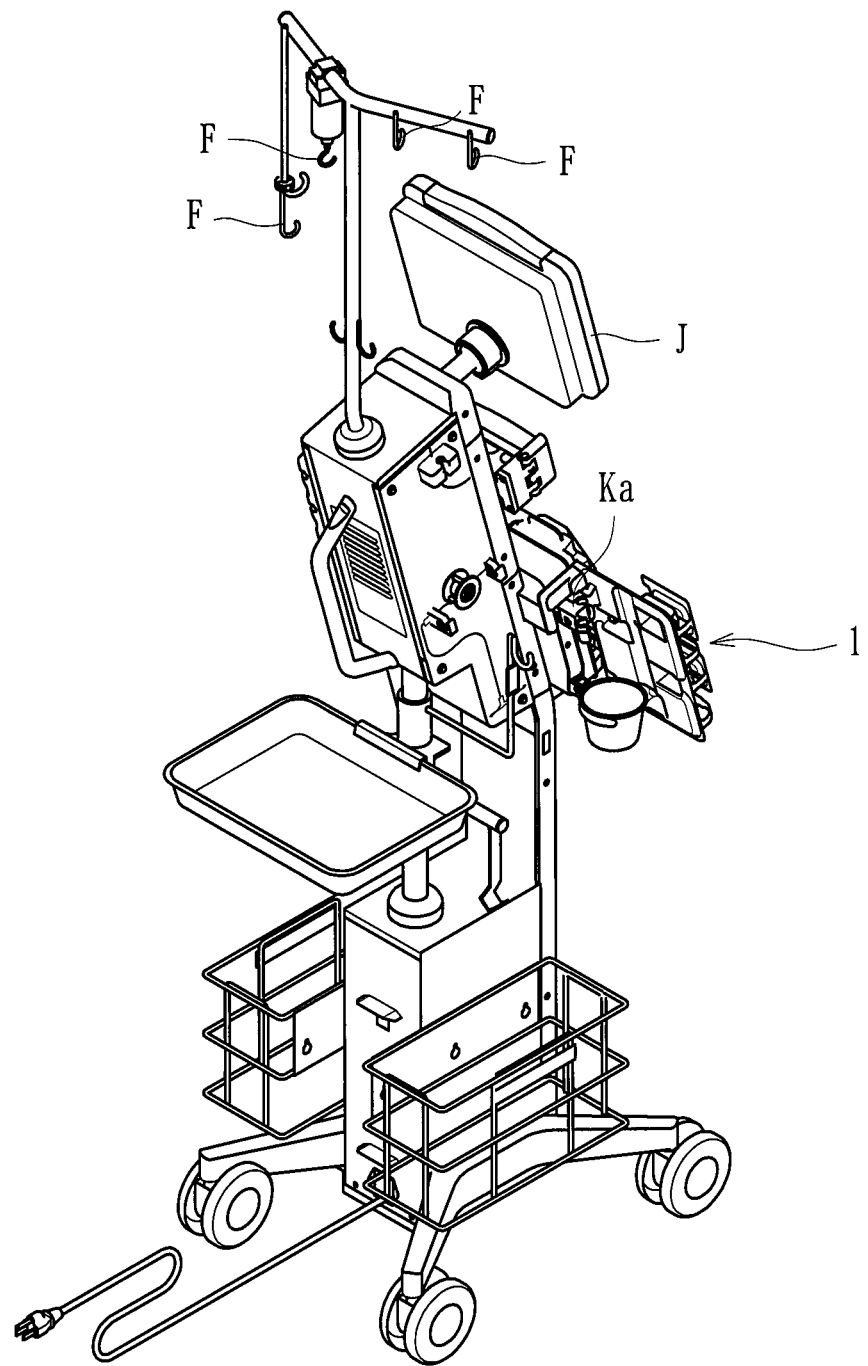

STORAGE TRAY

FIELD

The present teachings relate to a storage tray to be attached to a medical apparatus and in which a plurality of flexible tubes that each allow fluid to flow therethrough are stored.

BACKGROUND

A blood glucose controlling device according to a known proposal is configured as follows. While blood is collected from the body of a patient, the collected blood is diluted with a predetermined diluent and the blood sugar level of the blood is measured in real time by a blood-sugar-level-measurement device such as a glucose sensor. If the measured blood sugar level is too high, insulin is injected into the patient, whereby the blood sugar level is lowered. If the measured blood sugar level is too low, grape sugar (glucose) is injected into the patient, whereby the blood sugar level is raised.

Such a blood glucose controlling device is provided with, as disclosed by PTL 1 for example, a dilution device (a sampling device) for diluting the blood to be supplied to the blood-sugar-level-measurement device. A known dilution device is provided with a plurality of flexible tubes that allow different kinds of liquid, such as blood and diluent, to flow therethrough, respectively. Typically, such flexible tubes are distributed in units of several pieces that are packed in a resin storage bag. Therefore, to attach the flexible tubes packed in the bag to respective positions of the dilution device, the bag needs to be ripped off.

PTL 1: Japanese Unexamined Patent Application Publication No. 2013-245664.

SUMMARY

According to the above known technique, however, when the plurality of flexible tubes taken out of the storage bag and attached to a medical apparatus are charged by causing a priming solution (such as a physiological saline solution) to flow through those flexible tubes, the priming solution needs to be received by a separately provided container. Therefore, after such priming is finished, the storage bag in which the flexible tubes have been packed and the separately provided container in which the priming solution has been received need to be disposed of separately, which adversely affects working efficiency.

The present teachings have been conceived in view of the above circumstances and provides a storage tray in which flexible tubes are to be stored and with which the efficiency of work to be performed after priming can be improved.

According to the teachings herein, there is provided a storage tray that stores a flexible tube to be attached to a medical apparatus, the flexible tube allowing fluid to flow therethrough. The storage tray includes a tray body that is securable to a predetermined portion of the medical apparatus and in which the flexible tube is storable, and a receiving portion that is included in the tray body and is capable of receiving a priming solution and storing a predetermined volume of priming solution, the priming solution being used for flushing the flexible tube attached to the medical apparatus.

According to the teachings herein, in the storage tray taught herein, the flexible tube has a discharge portion from which the priming solution is dischargeable. Furthermore, in a state where the flexible tube is stored in the tray body, the discharge portion is set in a state where the priming solution is dischargeable into the receiving portion.

According to the teachings herein, in the storage tray taught herein, the discharge portion is provided with a cap that covers and protects the discharge portion. Furthermore, the cap is inserted into the receiving portion with the flexible tube stored in the tray body.

According to the teachings herein, in the storage tray taught herein, the receiving portion includes a covering portion that covers a storage space in which the priming solution is stored. Furthermore, the covering portion has an insertion hole into which the cap is inserted.

According to the teachings herein, in the storage tray taught herein, the tray body includes a securing portion that is capable of securing a predetermined portion of the medical apparatus such that the tray body is detachable from and attachable to the medical apparatus.

According to the teachings herein, in the storage tray taught herein, the tray body includes a storage portion in which each flexible tube is storable in a wound state.

According to the teachings herein, in the storage tray taught herein, the storage portion includes a spool part around which the flexible tube is windable to be stored, a fitting part in which an end portion of the flexible tube wound around the spool part is fittable and securable, and a lid part that covers the flexible tube wound around the spool part and prevents the flexible tube from coming off the spool part.

According to the teachings herein, in the storage tray taught herein, the storage portion has an indication showing a position of connection and/or an order of connection of the flexible tube wound around the spool part to the medical apparatus.

According to the teachings herein, the storage tray includes the tray body that is securable to the predetermined portion of the medical apparatus and in which the flexible tube is storable, and the receiving portion that is included in the tray body and is capable of receiving the priming solution and storing the predetermined volume of priming solution, the priming solution being used for flushing the flexible tube attached to the medical apparatus. Hence, not only the flexible tube can be stored, but the efficiency of the work to be performed after priming can also be improved.

According to the teachings herein, the flexible tube has the discharge portion from which the priming solution is dischargeable. Furthermore, in the state where the flexible tube is stored in the tray body, the discharge portion is set in the state where the priming solution is dischargeable into the receiving portion. Hence, during priming, the priming solution can be assuredly and smoothly discharged into and stored in the receiving portion.

According to the teachings herein, the discharge portion is provided with the cap that covers and protects the discharge portion. Furthermore, the cap is inserted into the receiving portion with the flexible tube stored in the tray body. Hence, the discharge portion can be protected by the cap, and the priming solution can be assuredly and smoothly discharged into and stored in the receiving portion during priming.

According to the teachings herein, the receiving portion includes the covering portion that covers the storage space in which the priming solution is stored. Furthermore, the covering portion has the insertion hole into which the cap is inserted. Hence, the priming solution discharged into the receiving portion can be prevented from scattering around the receiving portion. Moreover, the leakage of the priming solution from the receiving portion that may occur at the disposal of the tray body can be suppressed.

According to the teachings herein, the tray body includes the securing portion that is capable of securing the predetermined portion of the medical apparatus such that the tray body is detachable from and attachable to the medical apparatus. Hence, after the flexible tube is attached to the medical apparatus, the storage tray can be easily detached and disposed of.

According to the teachings herein, the tray body includes the storage portion in which each flexible tube is storable in the wound state. Hence, the flexible tubes can be attached to the medical apparatus by unwinding the flexible tubes that are in the wound state from the storage portions. Consequently, no binding tape or the like need to be provided separately.

According to the teachings herein, the storage portion includes the spool part around which the flexible tube is windable to be stored, the fitting part in which the end portion of the flexible tube wound around the spool part is fittable and securable, and the lid part that covers the flexible tube wound around the spool part and prevents the flexible tube from coming off the spool part. Hence, the flexible tube can be stored assuredly and in a compact size.

According to the teachings herein, the storage portion has the indication showing the position of connection and/or the order of connection of the flexible tube wound around the spool part to the medical apparatus. Hence, the work of attaching the flexible tube to the medical apparatus can be performed more smoothly and more assuredly.

BRIEF DESCRIPTION OF THE DRAWINGS

FIG. 1 is a schematic diagram illustrating a dilution device and a blood-sugar-level-measurement device to which a storage tray according to an embodiment of the present teachings are applied.

FIG. 2 is a schematic view illustrating an invasive catheter included in the dilution device.

FIG. 3 includes a front view and a bottom view of the storage tray.

FIG. 4 is a perspective view of the storage tray (with all lid portions thereof closed).

FIG. 5 is another perspective view of the storage tray (with all the lid portions thereof closed).

FIG. 6 is yet another perspective view of the storage tray (with one of the lid portions thereof open).

FIG. 7 is yet another perspective view of the storage tray (with one of the lid portions thereof open).

FIG. 8 includes a front view and a bottom view of the storage tray that is yet to be folded.

FIG. 9 is a front external view of the dilution device and the blood-sugar-level-measurement device (with the storage tray yet to be secured thereto) to which the storage tray is applied.

FIG. 10 is another front external view of the dilution device and the blood-sugar-level-measurement device (with the storage tray secured thereto) to which the storage tray is applied.

FIG. 11 is a rear external perspective view of the dilution device and the blood-sugar-level-measurement device (with the storage tray secured thereto) to which the storage tray is applied.

DETAILED DESCRIPTION

An embodiment of the present teachings will now be described specifically with reference to the drawings.

As illustrated in FIGS. 1 and 2, a dilution device A according to the embodiment is a medical device connected to a blood-sugar-level-measurement device S capable of measuring the level of blood sugar contained in blood. The dilution device A includes a multipump P including peristaltic pumps. The dilution device A is provided with a plurality of flexible tubes (L1 to L4). The dilution device A is intended to dilute the blood of a patient so that a glucose sensor T included in the blood-sugar-level-measurement device S can measure the blood sugar level. The dilution device A is included in a medical apparatus K that appears as illustrated in FIGS. 9 to 11.

The flexible tube L1 forms a liquid flow route with one end thereof connected to a storage bag B1 that stores a heparinized physiological saline solution, which is obtained by adding heparin (an anticoagulant) to a physiological saline solution, and with the other end thereof connected to an invasive catheter H. The flexible tube L2 forms a liquid flow route with one end thereof connected to the invasive catheter H and with the other end thereof connected to a mixing unit M, such as a chamber, included in the blood-sugar-level-measurement device S. The flexible tube L3 forms a liquid flow route with one end thereof connected to a storage bag B2 that stores a physiological saline solution and with the other end thereof connected to a predetermined position of the flexible tube L2. The flexible tubes L4 each form a liquid flow route with one end thereof connected to a storage bag B3 that stores a reference glucose solution and with the other end thereof connected to a predetermined position of a corresponding one of the flexible tube L1 and the flexible tube L2.

The invasive catheter H is connected to the distal end of the flexible tube L1 and to the distal end of the flexible tube L2 and is indwelling into the patient. The invasive catheter H allows the diluent in the storage bag B1 to be introduced thereinto while collecting the blood of the patient thereinto, and also allows a mixture of the blood and the diluent to be supplied into the mixing unit M of the blood-sugar-level-measurement device S. The mixing unit M is connected to the glucose sensor T of the blood-sugar-level-measurement device S. Hence, the diluted solution having been mixed substantially evenly in the mixing unit M is supplied to the glucose sensor T through flexible tubes L7 and L8.

With the supply of the physiological saline solution from the storage bag B2, the flexible tubes L1 to L10 and associated components provided to the dilution device A and to the blood-sugar-level-measurement device S can be charged (can undergo priming). Furthermore, with the supply of the reference glucose solution from the storage bag B3, the glucose sensor T measures the blood sugar level. Therefore, the glucose sensor T can be calibrated.

The multipump P allows the diluent and the blood to simultaneously flow at a predetermined ratio through the flexible tubes L1 and L2 attached thereto. The multipump P includes a plurality of rotors rotatable by respective motors, and rollers attached to the respective rotors and causing liquid to flow through the flexible tubes L1 and L2 by squeezing the flexible tubes L1 and L2. Note that flexible tubes L5, L6, and L9 included in the blood-sugar-level-measurement device S are also attached to the multipump P, and the flexible tubes L1, L2, L5, L6, and L9 are squeezed simultaneously, whereby the liquid is allowed to flow therethrough.

The blood-sugar-level-measurement device S includes the flexible tube L5 with one end thereof connected to a storage bag B4 storing the diluent and with the other end thereof connected to the mixing unit M, the flexible tube L6 with one end thereof being open to the atmosphere and with the other end thereof connected to the mixing unit M, the flexible tube L7 with one end thereof connected to the mixing unit M and with the other end thereof connected to a chamber N, the flexible tube L8 with one end thereof connected to the chamber N and with the other end thereof connected to the glucose sensor T, the flexible tube L9 with one end thereof connected to the glucose sensor T and with the other end thereof connected to a storage bag B5 storing waste liquid, and a flexible tube L10 with one end thereof connected to the chamber N and with the other end thereof connected to the storage bag B5.

The glucose sensor T continuously introduces the diluted blood of the patient that is supplied from the dilution device A onto an enzyme membrane and decomposes glucose contained in the diluted blood. When the glucose is decomposed, an electric current is generated. The glucose sensor T is capable of measuring the blood sugar level from the electric current. The glucose sensor T is connected to the drainage bag B5 with the flexible tube L9. The blood of the patient supplied to the mixing unit M through the flexible tube L2 (the blood diluted with the heparinized physiological saline solution) is further diluted with the diluent supplied through the flexible tube L5. Then, the blood sugar level of the diluted blood is measured by the glucose sensor T. The diluted blood is discharged into the drainage bag B5 through the flexible tube L9. Note that the mixing unit M is supplied with air through the flexible tube L6 so that blood and the diluent can be mixed in a good manner.

The plurality of flexible tubes L1 to L4 to be attached to the medical apparatus (in the embodiment, the medical apparatus K including the dilution device A and the blood-sugar-level-measurement device S) are stored in a storage tray 1 as illustrated in FIGS. 3 to 7. As illustrated in FIGS. 9 to 11, the medical apparatus K according to the embodiment includes a monitor J capable of displaying conditions of setting and so forth, hooks F on which the storage bags (B1 to B5) are hookable, and so forth. The medical apparatus K has a secured portion Ka at a predetermined position thereof.

The storage tray 1 according to the embodiment is securable to a predetermined portion (the secured portion Ka) of the medical apparatus K and includes, as illustrated in FIGS. 3 to 7, a tray body 2 in which the plurality of flexible tubes (L1 to L4) are storable, a receiving portion 3 provided at a lower peripheral portion of the tray body 2, and storage portions 4 to 7 provided at respective predetermined positions of the tray body 2. FIGS. 3 to 7 each illustrate a state where only the storage portion 7 is used for storing the flexible tube L1 (the other flexible tubes are attached to the medical apparatus K). In a stored state, the storage portions 4 to 6 are also used for storing the flexible tubes (L2 to L4), respectively.

As illustrated in FIG. 8, the storage tray 1 according to the embodiment is a resin molded member including various portions integrally formed together. The member is folded into a component including the receiving portion 3, a securing portion 11, and so forth. Specifically, a side peripheral portion of the tray body 2 is folded into an L shape, whereby a folded portion 2a is provided. Furthermore, a lower peripheral portion of the tray body 2 is folded and an extended portion 2b is inserted into a slit a, whereby the receiving portion 3 is provided. Furthermore, a covering portion 3a is folded, whereby the top of the receiving portion 3 is covered with the covering portion 3a.

The tray body 2 has the securing portion 11 that is capable of securing a predetermined portion of the medical apparatus K. Therefore, the tray body 2 is detachable from and attachable to the medical apparatus. Specifically, as illustrated in FIG. 8, the securing portion 11 is provided in the form of a cut that is made in the folded portion 2a, which is obtained by folding the side peripheral portion of the tray body 2 into an L shape. The storage tray 1 can be secured to the medical apparatus K (see FIGS. 10 and 11) by hooking the securing portion 11 on the secured portion Ka of the medical apparatus. The storage tray 1 can be detached from the medical apparatus K by unhooking the securing portion 11 from the secured portion Ka (see FIG. 9 for the detached state).

As illustrated in FIGS. 3 to 8, the storage portions 4 to 7 are each a portion capable of storing a corresponding one of the flexible tubes (L1 to L4) in a wound state. The flexible tube L3 (a flushing line) is stored in the storage portion 4, the flexible tube L1 (a heparinized-physiological-saline-solution line) is stored in the storage portion 5, the flexible tubes L4 (calibration lines) are stored in the storage portion 6, and the flexible tube L2 (a patient line) is stored in the storage portion 7. The storage portions 4 to 7 according to the embodiment each include a spool part 8, a fitting part 9, and a lid part 10.

More specifically, the spool part 8 is a projected portion around which the flexible tube (one of L1 to L4) is windable to be stored. The fitting part 9 is provided in the upper surface of the spool part 8. An end portion of the flexible tube (one of L1 to L4) that is wound around the spool part 8 is fittable into and securable in the fitting part 9. That is, the fitting part 9 is a groove having substantially the same shape and size as the end portion of the flexible tube (one of L1 to L4) so that the fitting part 9 can receive and secure the end portion of the flexible tube (one of L1 to L4) that is wound around the spool part 8.

Furthermore, the storage portions (4 to 7) according to the embodiment each have an indication showing the position of connection of the corresponding one of the flexible tubes (L1 to L4) that is wound around the spool part 8 to the medical apparatus K (a corresponding one of character strings saying "FLUSHING LINE," "HEPARINIZED-PHYSIOLOGICAL-SALINE-SOLUTION LINE," "CALIBRATION LINE," and "PATIENT LINE") and the order of connection (a corresponding one of numbers (1) to (4)). In the embodiment, the position of connection and the order of connection are provided on the lid part 10. Alternatively, the position of connection and the order of connection may be provided on another position (any portion corresponding to each of the storage portions 4 to 7). Moreover, only one of the position of connection and the order of connection may be provided.

As illustrated in FIG. 8, the lid part 10 is a flat part provided at an end of an extended portion 10c extended from a side periphery of the tray body 2. As illustrated in FIGS. 3 to 7, the lid part 10 covers the flexible tube (one of L1 to L4) wound around the spool part 8 and thus prevents the flexible tube (one of L1 to L4) from coming off the spool part. That is, the lid parts 10 are provided at respective positions in correspondence with the spool parts 8, and projections 10a of each of the lid part 10 are fitted into and thus secured in respective recesses 8a provided in a corresponding one of the spool parts 8. Thus, the lid parts 10 cover the flexible tubes (L1 to L4) wound around the spool parts 8 and retain the flexible tubes (L1 to L4) in the wound state.

As illustrated in FIGS. 3 to 8, the receiving portion 3 included in the tray body 2 is a container-like portion capable of receiving a priming solution and storing a predetermined volume of priming solution. The priming solution is used for flushing the flexible tubes (L1 to L4) attached to the medical apparatus K. The predetermined volume may be determined appropriately on the basis of, for example, the volume of priming solution that is discharged from a discharge portion when the flexible tubes (L1 to L4) are flushed. In the embodiment, the priming solution in the flexible tube L1 is dischargeable from the discharge portion (the distal end at which the invasive catheter H is attached). In a state where the flexible tube L1 is stored in the tray body 2, the discharge portion is set in a state where the priming solution is dischargeable into the receiving portion 3.

Specifically, a cap 12 for covering and protecting the discharge portion of the flexible tube L1 is attached to the discharge portion. With the flexible tube L1 stored in the tray body 2 (that is, in a state where the flexible tube L1 is stored in the storage portion 7), the cap 12 is inserted into the receiving portion 3. Furthermore, the receiving portion 3 according to the embodiment includes the covering portion 3a that covers a storage space in which the priming solution is stored, and the covering portion 3a has an insertion hole 3aa into which the cap 12 is inserted. Hence, the priming solution supplied during priming (in the embodiment, the physiological saline solution supplied from the storage bag B2) flows through the flexible tubes (L1 to L4) and through the cap 12 and is received by the receiving portion 3.

The embodiment employs the tray body 2 that is securable to a predetermined portion of the medical apparatus K and in which the flexible tubes (L1 to L4) are storable, and the receiving portion 3 that is included in the tray body 2 and is capable of receiving the priming solution, which is used for flushing the flexible tubes (L1 to L4) attached to the medical apparatus K, and storing a predetermined volume of priming solution. Therefore, not only the flexible tubes (L1 to L4) can be stored, but the efficiency of the work to be performed after priming can also be improved. This means as follows. The priming solution is storable in the receiving portion 3 during priming. Therefore, after the priming is finished, the tray body 2 with all of the flexible tubes (L1 to L4) removed from the storage portions (4 to 7) thereof can be disposed of simultaneously with the priming solution. Thus, the working efficiency can be improved.

According to the embodiment, in the state where the flexible tubes (L1 to L4) are stored in the tray body 2, the discharge portion of the flexible tube L1 from which the priming solution is dischargeable is set in a state where the priming solution is dischargeable into the receiving portion 3. Therefore, during priming, the priming solution can be assuredly and smoothly discharged into and stored in the receiving portion. In particular, according to the embodiment, the cap 12 for covering and protecting the discharge portion of the flexible tube L1 is provided, and the cap 12 is inserted into the receiving portion 3 with the flexible tubes (L1 to L4) stored in the tray body 2. Therefore, the discharge portion can be protected by the cap 12, and the priming solution can be assuredly and smoothly discharged into and stored in the receiving portion 3 during priming.

Furthermore, the receiving portion 3 according to the embodiment includes the covering portion 3a that covers the storage space in which the priming solution is stored, and the covering portion 3a has the insertion hole 3aa into which the cap 12 is inserted. Therefore, the priming solution discharged into the receiving portion 3 can be prevented from scattering around the receiving portion 3. Moreover, the leakage of the priming solution from the receiving portion 3 that may occur at the disposal of the tray body 2 can be suppressed.

Furthermore, the tray body 2 according to the embodiment includes the securing portion 11 that is capable of securing a predetermined portion (the secured portion Ka) of the medical apparatus K, whereby the tray body 2 is detachable from and attachable to the medical apparatus K. Therefore, after the flexible tubes (L1 to L4) are attached to the medical apparatus K, the storage tray 1 can be easily detached and disposed of. Furthermore, the tray body 2 includes the storage portions (4 to 7) in which the respective flexible tubes (L1 to L4) are storable in the wound state. Therefore, the flexible tubes can be attached to the medical apparatus by unwinding the flexible tubes that are in the wound state from the storage portions. Consequently, no binding tape or the like need to be provided separately.

Furthermore, the storage portions (4 to 7) each include the spool part 8 around which a corresponding one of the flexible tubes (L1 to L4) is windable to be stored, the fitting part 9 in which the end portion of the flexible tube (one of L1 to L4) that is wound around the spool part 8 is fittable and thus securable, and the lid part 10 that covers the flexible tube (one of L1 to L4) wound around the spool part 8 and thus prevents the flexible tube (one of L1 to L4) from coming off the spool part 8. Therefore, the flexible tubes (L1 to L4) can be stored assuredly and in a compact size. Moreover, the storage portions 4 to 7 each have an indication showing the position of connection or the order of connection of a corresponding one of the flexible tubes (L1 to L4) wound around the respective spool parts 8 to the medical apparatus K. Therefore, the work of attaching the flexible tubes (L1 to L4) to the medical apparatus K can be performed more smoothly and more assuredly.

While an embodiment of the present teachings have been described above, the present teachings are not limited thereto. For example, the storage tray may store any number of flexible tubes other than four, or the storage tray may store only one flexible tube. Furthermore, according to the embodiment, the tray body 2 in which the flexible tubes (L1 to L4) are stored is attached to the medical apparatus K. Then, after the priming is finished, the tray body 2 is detached from the medical apparatus K and is disposed of. Alternatively, the tray body 2 may be kept attached to the medical apparatus K. In addition, the medical apparatus K to which the flexible tubes (L1 to L4) are to be attached may be in any mode.

The storage tray according to the present teachings may have any other external shape or any other additional functions, as long as the storage tray includes a tray body that is securable to a predetermined portion of a medical apparatus and in which flexible tubes are storable, and a receiving portion that is included in the tray body and is capable of receiving and storing a predetermined volume of priming solution that is used for flushing the flexible tubes attached to the medical apparatus.

REFERENCE SIGNS LIST 1 storage tray
2 tray body
3 receiving portion
4 to 7 storage portion
8 spool part
9 fitting part
10 lid part
11 securing portion
K medical apparatus

The invention claimed is:

1. A storage tray that stores a flexible tube to be attached to a medical apparatus, the flexible tube allowing fluid to flow therethrough, the storage tray comprising:
   a tray body that is securable to a predetermined portion of the medical apparatus and in which the flexible tube is storable; and
   a receiving portion that is included in the tray body and is capable of receiving a priming solution and storing a predetermined volume of priming solution, the priming solution being used for flushing the flexible tube attached to the medical apparatus; and
   wherein the flexible tube connects a storage bag and the receiving portion so that priming solution extends from the storage bag through the flexible tube, flushing the flexible tube, and into the receiving portion; and
   wherein the receiving portion includes a covering portion that covers a storage space in which the priming solution is stored, and
   wherein the covering portion has an insertion hole into which a cap is inserted; wherein the storage tray includes storage portions capable of storing one of the flexible tubes in a wound state and the storage portions include a spool part, a fitting part, and a lid part; wherein the one of the flexible tubes are windable around the spool part; wherein the fitting part is located on an upper surface of the spool part and the fitting part is substantially a same shape and size as an end portion of the flexible tube so that the fitting part receives and secures the end portion of the one of the flexible tubes that is wound around the spool part.

2. The storage tray according to claim 1, wherein the flexible tube has a discharge portion from which the priming solution is dischargeable, and wherein in a state where the flexible tube is stored in the tray body, the discharge portion is set in a state where the priming solution is dischargeable into the receiving portion.

3. The storage tray according to claim 1, wherein the tray body includes a securing portion that is capable of securing a predetermined portion of the medical apparatus such that the tray body is detachable from and attachable to the medical apparatus.

4. The storage tray according to claim 1, wherein the tray body includes a storage portion in which each flexible tube is storable in a wound state.

5. The storage tray according to claim 4, wherein the storage portion includes a spool part around which the flexible tube is windable to be stored, a fitting part in which an end portion of the flexible tube wound around the spool part is fittable and securable, and a lid part that covers the flexible tube wound around the spool part and prevents the flexible tube from coming off the spool part.

6. The storage tray according to claim 1, wherein the storage tray includes calibration lines.

7. The storage tray according to claim 1, wherein the storage tray is a resin molded member.

8. The storage tray according to claim 1, wherein the tray body includes a receiving portion and a securing portion that are folded relative to one another.

9. The storage tray according to claim 8, wherein a side peripheral portion of the tray body is folded into an L shape.

10. The storage tray according to claim 1, wherein the storage tray includes a securing portion that is configured to hook on a securing portion of a medical apparatus.

11. The storage tray according to claim 1, wherein the storage portions are four storage portions.

12. The storage tray according to claim 11, wherein the four storage portions are a flushing line storage portion, a calibration line storage portion, a patient line storage portion, and a saline solution line storage portion.

13. A storage tray that stores a flexible tube to be attached to a medical apparatus, the flexible tube allowing fluid to flow therethrough, the storage tray comprising:
   a tray body that is securable to a predetermined portion of the medical apparatus and in which the flexible tube is storable; and
   a receiving portion that is included in the tray body and is capable of receiving a priming solution and storing a predetermined volume of priming solution, the priming solution being used for flushing the flexible tube attached to the medical apparatus;
   wherein the flexible tube has a discharge portion from which the priming solution is dischargeable, and wherein in a state where the flexible tube is stored in the tray body, the discharge portion is set in a state where the priming solution is dischargeable into the receiving portion;
   wherein the discharge portion is provided with a cap that covers and protects the discharge portion, and wherein the cap is inserted into the receiving portion with the flexible tube stored in the tray body;
   wherein the receiving portion includes a covering portion that covers a storage space in which the priming solution is stored, and
   wherein the covering portion has an insertion hole into which the cap is inserted.

14. The storage tray according to claim 13, wherein the tray body includes a securing portion that is capable of securing a predetermined portion of the medical apparatus such that the tray body is detachable from and attachable to the medical apparatus.

15. The storage tray according to claim 14, wherein the tray body includes a storage portion in which each flexible tube is storable in a wound state.

16. A storage tray that stores a flexible tube to be attached to a medical apparatus, the flexible tube allowing fluid to flow therethrough, the storage tray comprising:
   a tray body that is securable to a predetermined portion of the medical apparatus and in which the flexible tube is storable; and
   a receiving portion that is included in the tray body and is capable of receiving a priming solution and storing a predetermined volume of priming solution, the priming solution being used for flushing the flexible tube attached to the medical apparatus; and
   wherein the flexible tube connects a storage bag and the receiving portion so that priming solution extends from the storage bag through the flexible tube, flushing the flexible tube, and into the receiving portion;
   wherein the tray body includes a storage portion in which each flexible tube is storable in a wound state;
   wherein the storage portion includes a spool part around which the flexible tube is windable to be stored, a fitting part in which an end portion of the flexible tube wound around the spool part is fittable and securable, and a lid part that covers the flexible tube wound around the spool part and prevents the flexible tube from coming off the spool part; and
   wherein the storage portion has an indication showing a position of connection and/or an order of connection of the flexible tube wound around the spool part to the medical apparatus.

* * * * *